United States Patent [19]
Yatvin et al.

[11] Patent Number: 5,149,794
[45] Date of Patent: Sep. 22, 1992

[54] COVALENT LIPID-DRUG CONJUGATES FOR DRUG TARGETING

[75] Inventors: Milton B. Yatvin, Portland, Oreg.; David W. Parks, Seattle, Wash.; Ronald W. McClard, Portland, Oreg.; Michael H. B. Stowell, Salt Lake City, Utah; John F. Witte, Portland, Oreg.

[73] Assignee: State of Oregon, Portland, Oreg.

[21] Appl. No.: 607,982

[22] Filed: Nov. 1, 1990

[51] Int. Cl.$^5$ .................. C07H 17/00; A61K 37/22; A61K 31/70

[52] U.S. Cl. ............... 536/29; 424/450; 514/51; 514/78; 530/300; 530/331; 530/329; 544/243; 564/153

[58] Field of Search ........... 424/450; 514/78, 946, 514/943, 557, 51; 260/389, 404, 313; 536/29

[56] References Cited

PUBLICATIONS van Wijk et al., 1991, Biochim. Biophys. Acta 1084: 307–310.
Hostetler et al., 1990, J. Biol. Chem. 265: 6112–6117.
Steim et al., 1990, Biochem. Biophys. Res. Commun. 171: 451–457.
Neto et al., 1990, Biochem. Biophys. Res. Commun. 171: 458–464.
Krowka et al., 1990, J. Immunol. 144: 2535–2540.
Loughery et al., 1990, J. Immunol. Methods 132: 25–35.
Comiskey & Heath, 1990, Biochim. Biophys. Acta 1024: 307–317.
Brown & Silvius, 1990, Biochim. Biophys. Acta 1023: 341–351.
MacDonald, 1990, J. Biol. Chem. 265: 13533–13539.
Ng & Heath, 1989, Biochim. Biophys. Acta 981: 261–268.
Nothnagel, 1989, Biochim. Biophys. Acta 980: 209–219.
Afzelius et al., 1989, Biochim. Biophys. Acta 979: 231–238.
Dreyer et al., 1989, Proc. Natl. Acad. Sci. USA 86: 9752–9756.
Koval & Pagano, 1989, J. Cell Biol. 108: 2169–2181.
Brewster et al., 1988, J. Pharm. Sci. 77: 981–985.
Heath, 1987, Methods in Enzymol. 149: 111–119.
Kinsky & Loeder, 1987, Biochim. Biophys. Acta 921: 96–103.
Kinsky et al., 1987, Biochim. Biophys. Acta 917: 211–218.
Jacobson et al., 1987, FEBS Lett. 255: 97–102.
Berdel et al., 1987, Lipids 22: 943–946.
Rosenberg et al., 1987, J. Neurochem. 48: 865–875.
Debs et al., 1987, Biochim. Biophys. Acta 901: 183–190.
Salord et al., 1986, Biochim. Biophys. Acta 886: 64–75.
Kinsky et al. 1986, Biochim. Biophys. Acta 885: 129–135.
Kung & Redemann, 1986, Biochim. Biophys. Acta 862: 435–439.
Heath et al., 1986, Biochim. Biophys. Acta 862: 72–80.
Heath & Martin, 1986, Chem. Phys. Lipids 40: 347–358.
Hashimoto et al., 1985, Biochim. Biophys. Acta 816: 163–168.
Hashimoto et al., 1985, Biochim. Biophys. Acta 816: 169–178.
Pagano et al., 1983, J. Biol. Chem. 258: 2034–2040.
Rahman et al., 1982, Life Sci. 31: 2061–2071.
Verbloom et al., 1981, Synthesis 1032: 807–809.
Matsuura et al., 1976, J. Chem. Soc. Chem. Comm. pp. 451–452.
Kishimoto, 1975, Chem. Phys. Lipids 15: 33–36.
Anderson et al., 1963, J. Am. Chem. Soc. 85: 3039.
Remy et al., 1962, J. Org. Chem. 27 2491–2500.
Mukhergee & Heidelberger, 1962, Cancer Res. 22: 815–822.
Paul & Anderson, 1960, J. Am. Chem. Soc. 82: 4596–4600.
Smith and Khorana, 1958, J. Am. Chem. Soc. 80: 1141–1145.
Baer, 1955, Can. J. Biochem. Phys. 34: 288–304.

*Primary Examiner*—John W. Rollins
*Attorney, Agent, or Firm*—Allegretti & Witcoff, Ltd.

[57] ABSTRACT

This invention relates to a novel method of drug targeting which comprises covalently binding a drug to a lipid carrier. This composition has the unique ability to both enhance the rate at which an antineoplastic or antiviral drug crosses the plasma membrane, and to direct the drug within the cell to specific organelles. The versatility of these conjugates may be further enhanced by including a spacer group between the drug and the lipid which may act to modulate drug release at the target site.

10 Claims, 9 Drawing Sheets

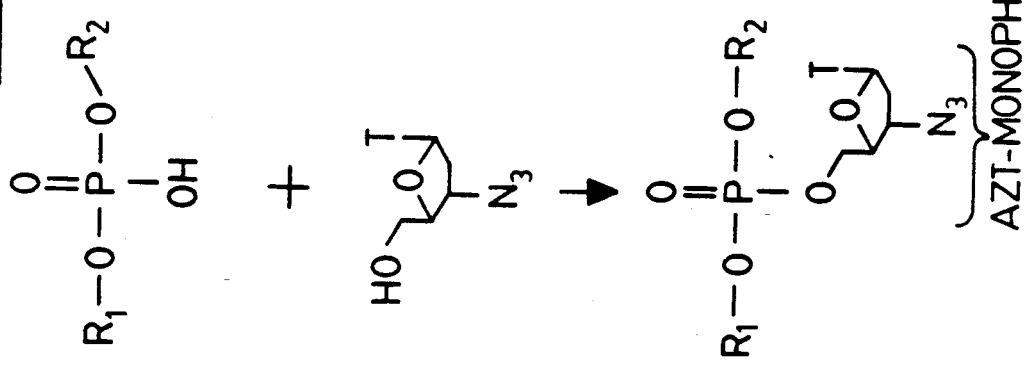
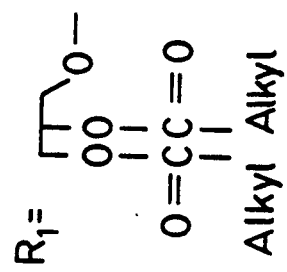
FIG. 6

COVALENT LIPID-DRUG CONJUGATES FOR DRUG TARGETING

This invention was made with government support under CA 24872 and GM 31459 awarded by the National Institutes of Health. The government has certain rights in the invention.

BACKGROUND OF THE INVENTION

The invention herein describes a method of facilitating the entry of drugs into cells at pharmokinetically useful levels and also a method of targeting drugs to specific organelles within the cell. This lipid/drug conjugate targeting invention embodies an advance over other drug targeting methods because through this method, intracellular drug concentrations may reach levels which are orders of magnitude higher than those achieved otherwise. Furthermore, it refines the drug delivery process by allowing therapeutic agents to be directed to certain intracellular structures. This technology is appropriate for use with antiviral and antineoplastic drugs because it has been observed that both virally infected and neoplastic cells have an altered intracellular organelle morphology.

Numerous methods for enhancing the activity and specificity of antiviral and antineoplastic drug action have been proposed. In general, the desired result is to increase both the efficiency and specificity of the therapeutic agent. One method of achieving this result has been receptor targeting. This method involves linking the therapeutic agent to a ligand which has an affinity for a receptor expressed on the desired target cell. Treatment by this method results in the drug adhering to the target cell through the ligand receptor complex and exerting its therapeutic effects directly on the cell.

One drawback of receptor targeting lies in the finite number of receptors on target cells. It has been estimated that the maximum number of receptors on a cell is approximately one million (Darnell, Lodish and Baltimore, *Molecular Cell Biology* (1986)). Thus, there is a maximum binding of one million drug ligand complexes to any given cell. Furthermore, the maximum number of specific receptors is much lower, for example, for a specific steroid, there are between ten thousand and one hundred thousand. Id. Thus, attempts at receptor targeting wherein the drug is conjugated with a ligand specific for a single receptor type will result in a maximum binding of less than about one hundred thousand conjugates per cell.

In response to the deficiencies encountered with receptor targeting, investigators have looked for other methods of delivering therapeutic agents at concentrations higher than those achievable through the receptor targeting process. Experiments suggested that lipids have selective affinities for specific biological membranes.

The selective association of certain lipids with specific biological membranes provided a possible avenue of drug targeting. In light of this possibility, researchers have attempted to target drugs by conjugating them with cholesterol. Unfortunately, these attempts have met with disappointing results. Remy et al., 1962, J. Org. Chem. 27:2491–2500. Mukhergee, K. L., Heidelberger, C., 1962, Cancer Research 22:815–22. Brewster, M. E., et al., Improved delivery through biological membranes. XXXL: Solubilization and stabilization of an estradiol chemical delivery system by modified beta-cyclodextrins, J. Pharm. Sci. 77:981–985, have had some success with carrying estradiol to the brain using pyridinium salts as carriers.

Another attempt at cell targeting through the use of lipids was made by Rahman et al., 1982, Life Sci. 31:2061–71. These investigators found that liposomes which contained galactolipid as part of the lipid appeared to have a higher affinity for parenchymal cells than liposomes which lacked galactolipid. These researchers suggested that this finding might have utility in drug targeting.

An additional challenge in designing an appropriate drug delivery scheme is to include within the drug conjugate a functionality which could either accelerate or reduce the rate at which the drug is released upon arrival at the desired site. Such a functionality would be especially valuable if it allowed differential rates of drug release.

BRIEF SUMMARY OF THE INVENTION

The present invention is directed to an improved method for drug delivery. This drug delivery system achieves site specific drug delivery through conjugating the drug with a lipid carrier. This invention also has the specific advantage of facilitating the entry of drugs into cells via a lipid carrier, allowing intracellular drug concentrations to attain levels higher than the levels achievable by other methods. As disclosed herein, the invention comprehends a lipid drug conjugate wherein the lipid will selectively associate with certain biological membranes, and facilitate intracellular drug localization. The lipid may be conjugated to the drug through use of a spacer, which may act to release the drug from the lipid, target the conjugate to the cell, incorporate the drug into a viral envelope, or perform other functions to maximize the effectiveness of the drug.

This type of conjugate has numerous advantages. First, this invention will allow the entry of drugs into cells at a pharmokinetical rate not currently possible with many potentially useful antiviral and antineoplastic drugs. Second, in comparison to receptor specific drug targeting this method will not require specific receptors. Third, it is believed that a therapeutic ratio between normal and either virally infected or neoplastic cells will be obtained as a result of greater cell sensitivity due to the presence of already compromised organelles, such as the golgi. Fourth, in contrast to tradional attempts to target drugs to specific cells, this method may target drugs to intracellular compartments and organelles. Fifth, these compounds may be incorporated into the viral envelope directly modifying its lipid composition, which could influence infectivity. Sixth, this invention incorporates a spacer region which can be varied and may allow a pharmacologically relevant rate of drug release from lipids.

BRIEF DESCRIPTION OF THE DRAWINGS

FIG. 6 depicts the synthetic scheme put forth in Example 6.

DETAILED DESCRIPTION OF THE PREFERRED EMBODIMENTS

Figure 1:
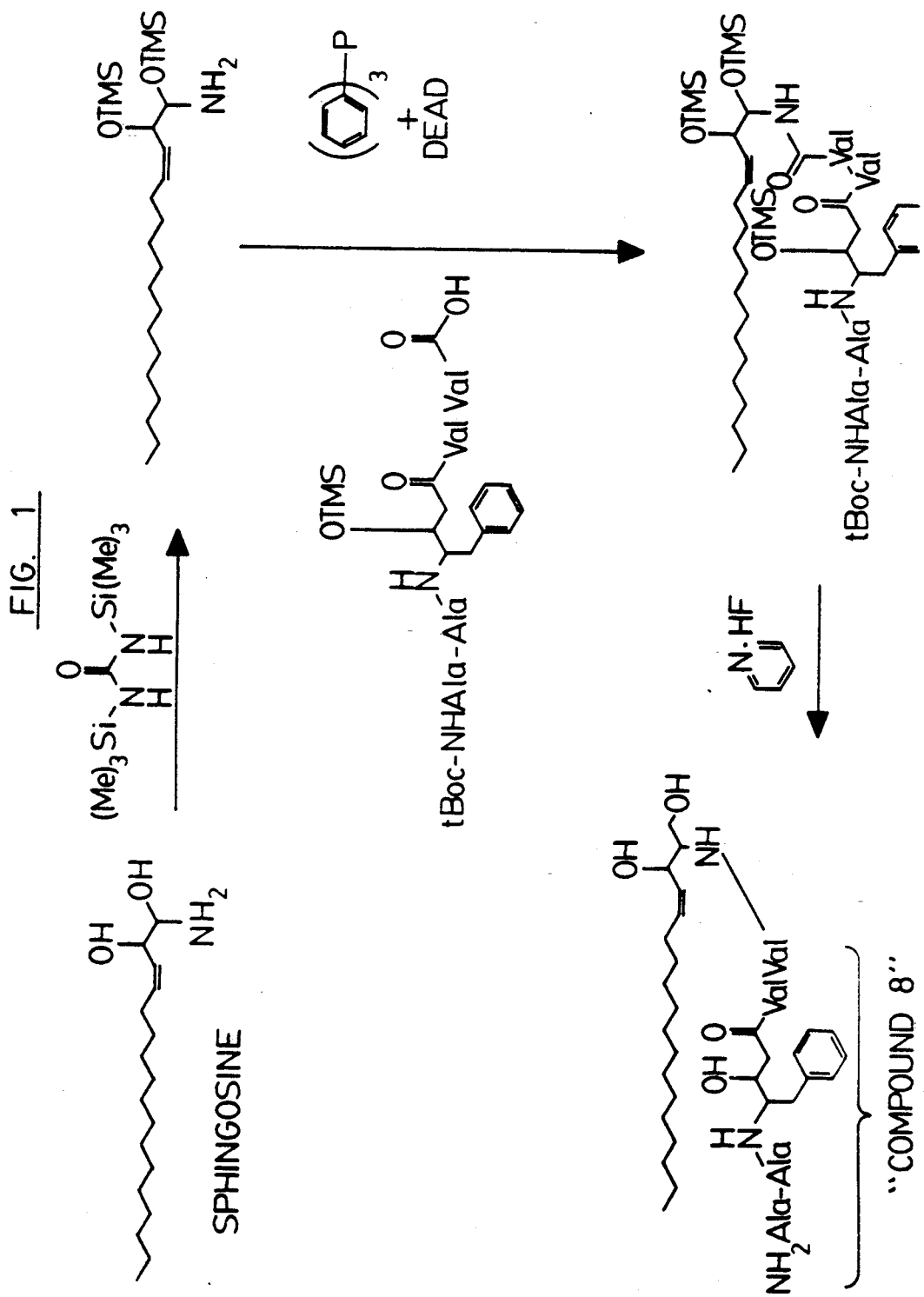
FIG. 1 depicts the synthetic scheme put forth in Example 1.
Figure 2:
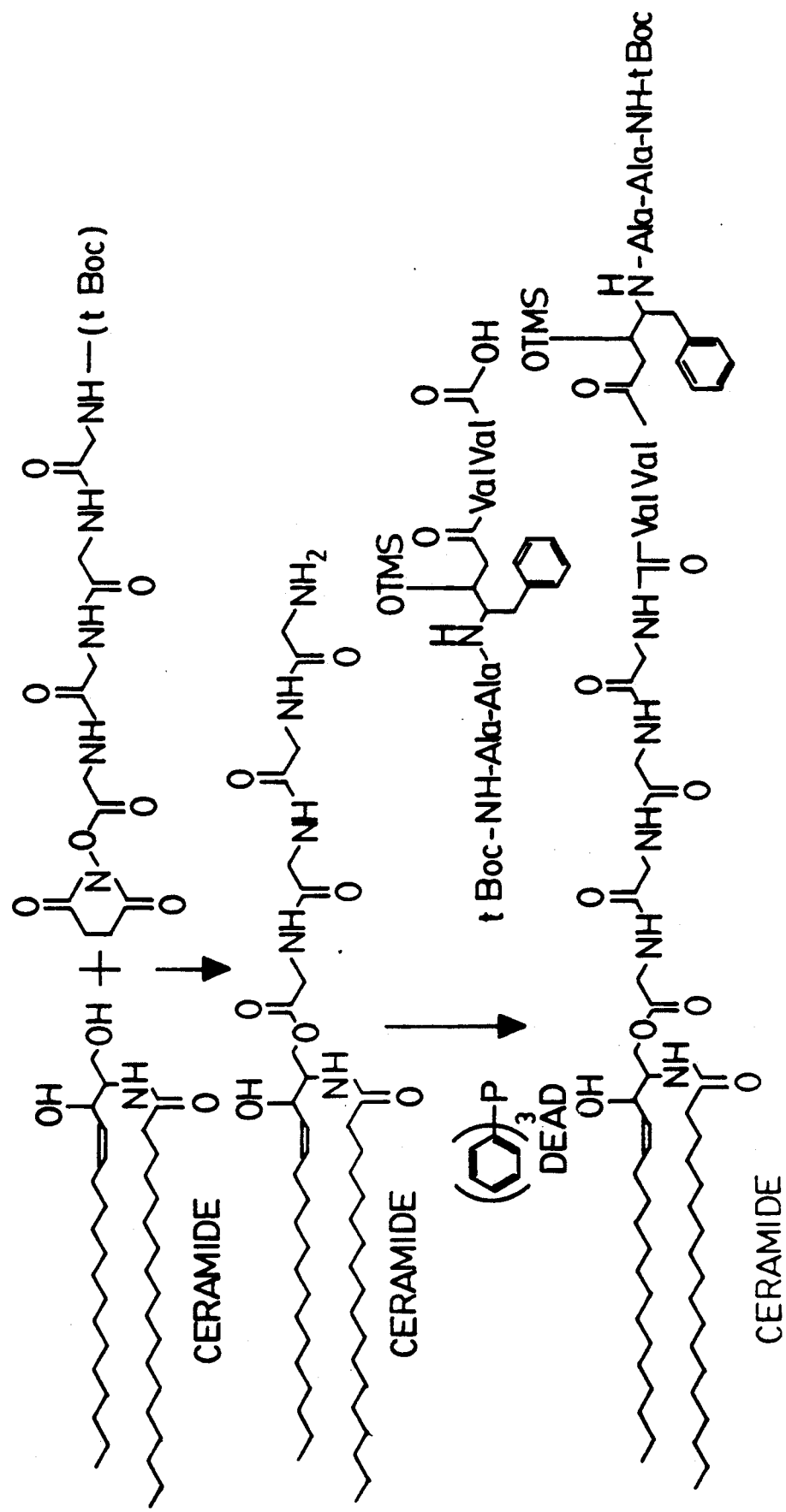
FIG. 2 depicts the synthetic scheme put forth in Example 2.
Figure 2:
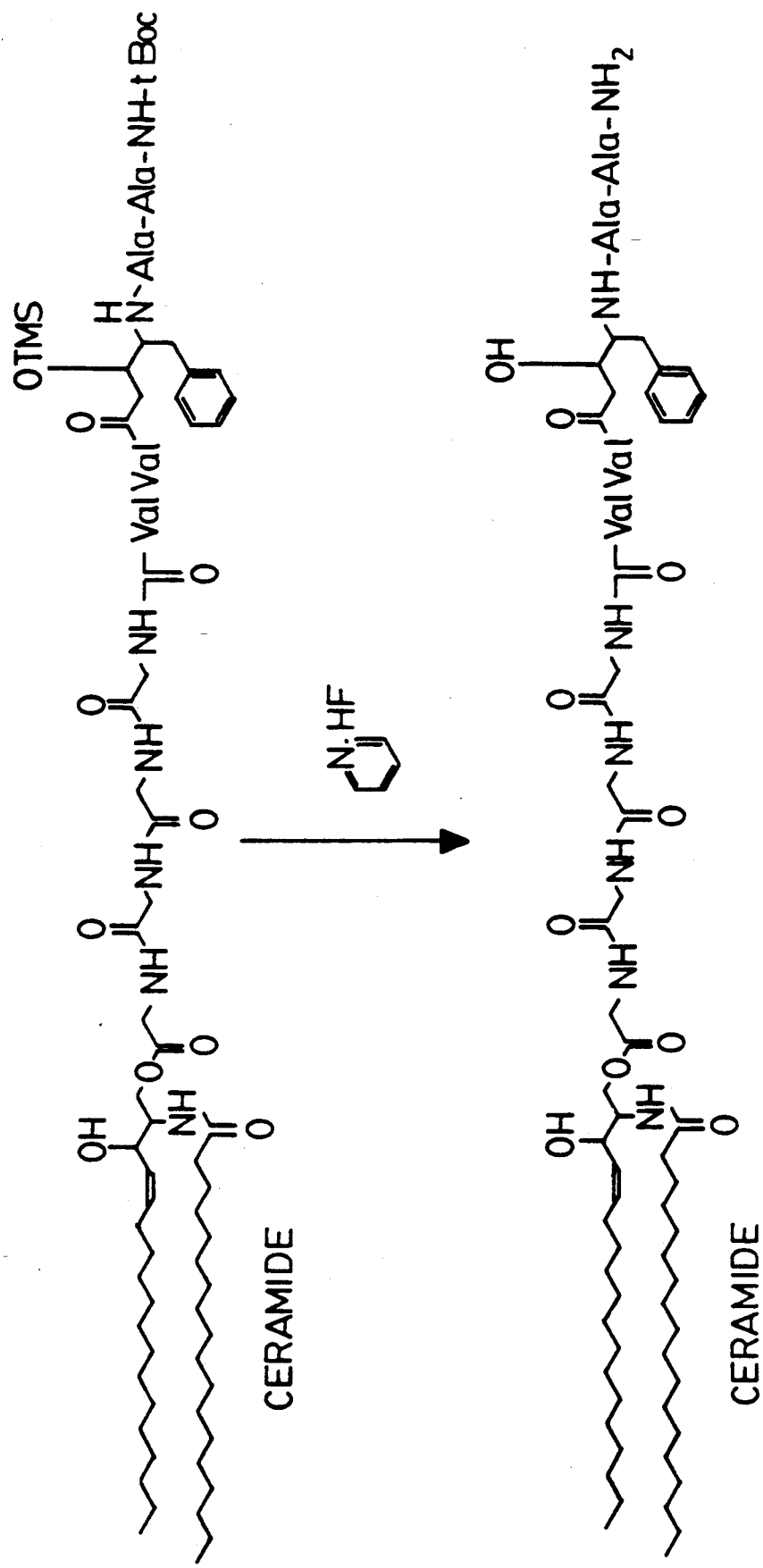
Figure 3:
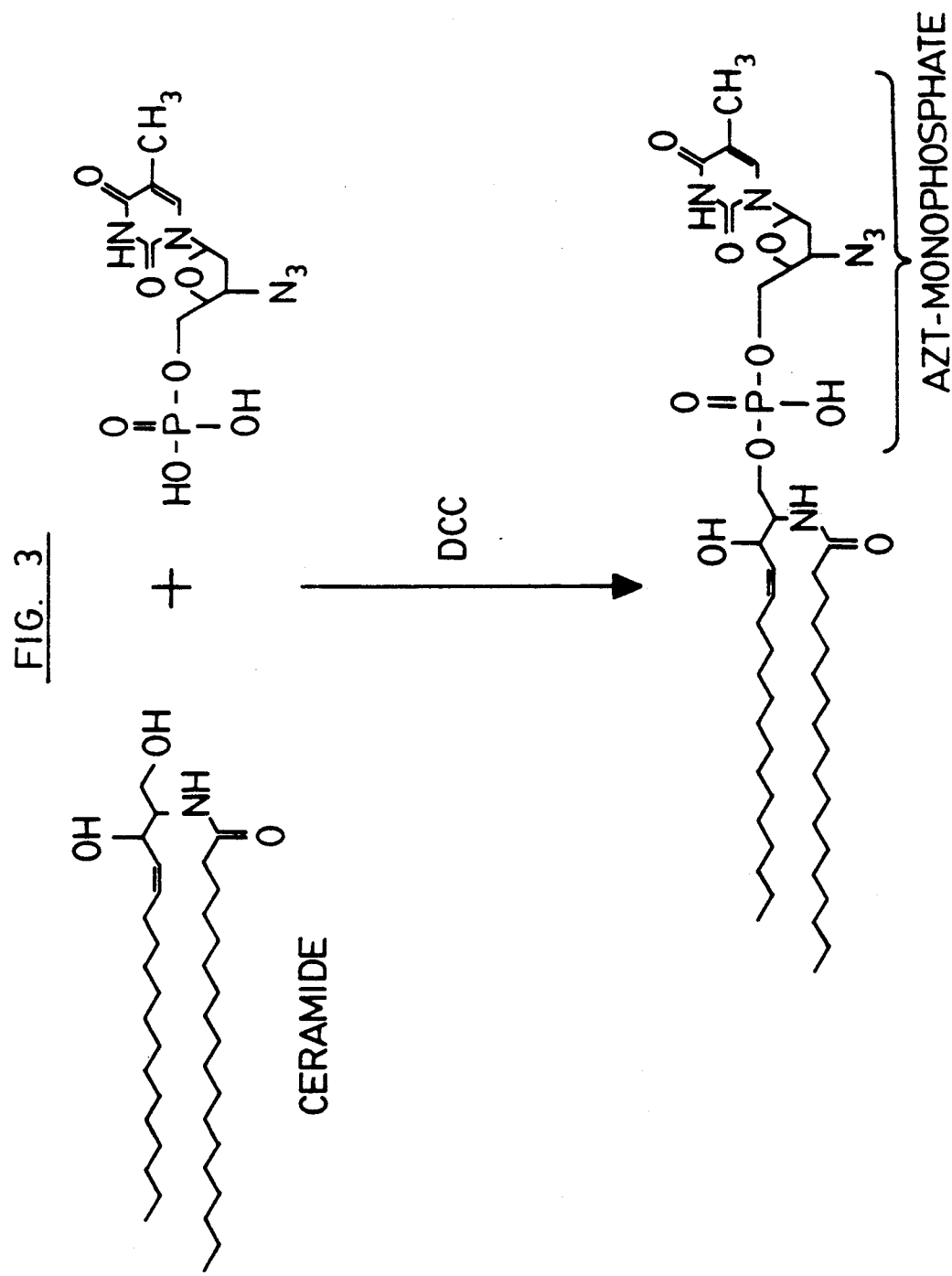
FIG. 3 depicts the synthetic scheme put forth in Example 3.
Figure 4:
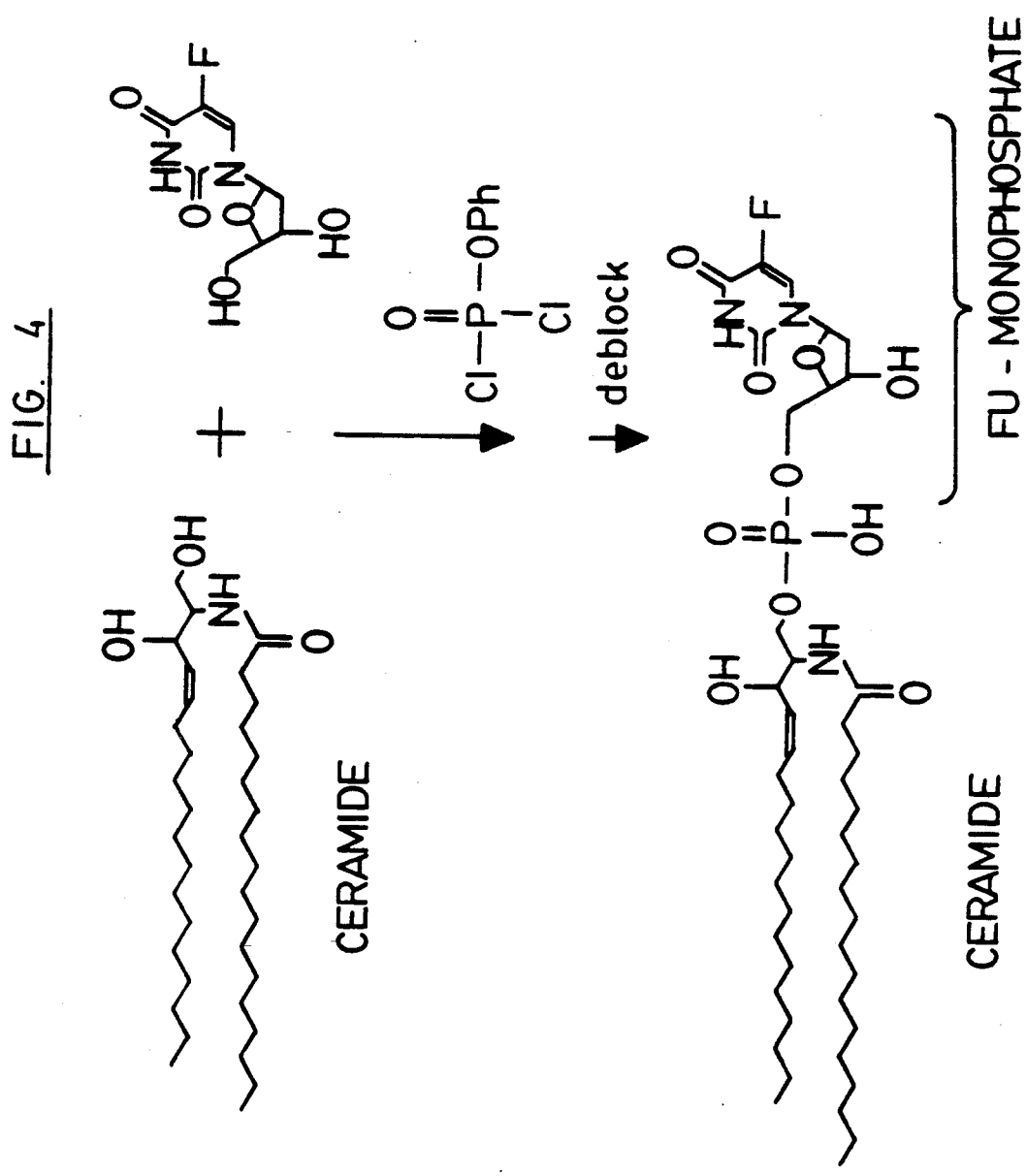
FIG. 4 depicts the synthetic scheme put forth in Example 4.
Figure 5:
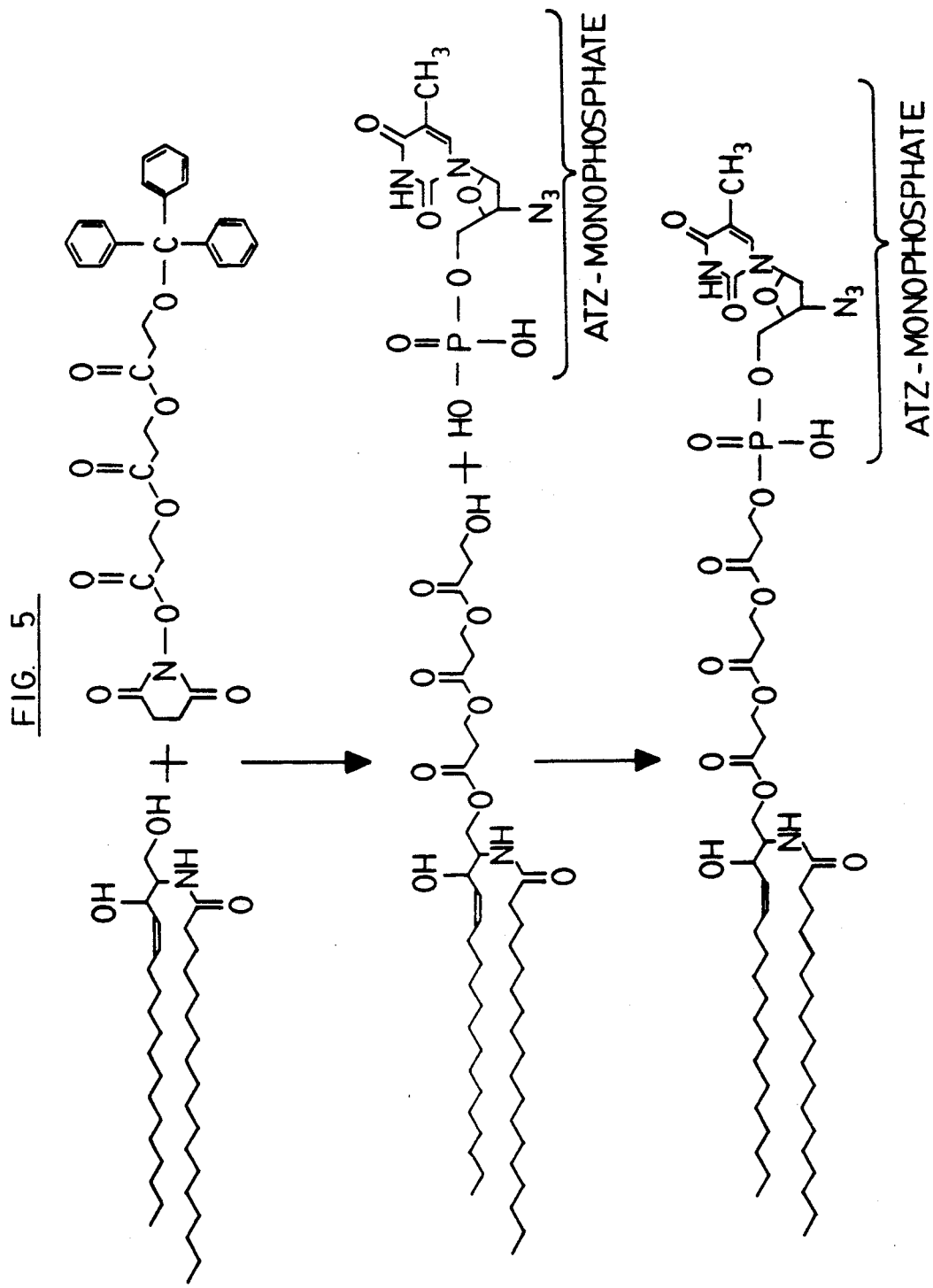
FIG. 5 depicts the synthetic scheme put forth in Example 5.
Figure 7:
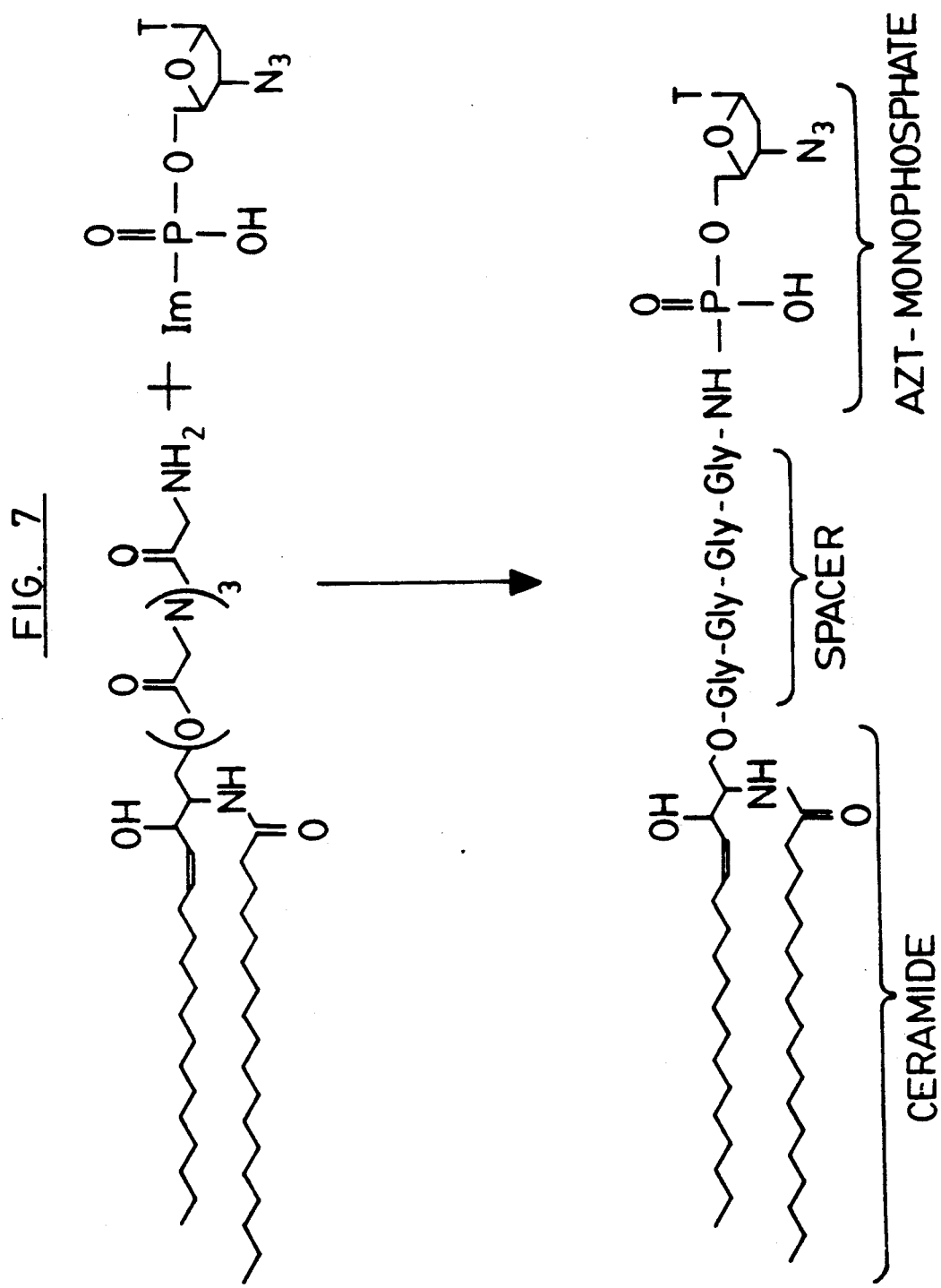
FIG. 7 depicts the synthetic scheme put forth in Example 7.
Figure 8:
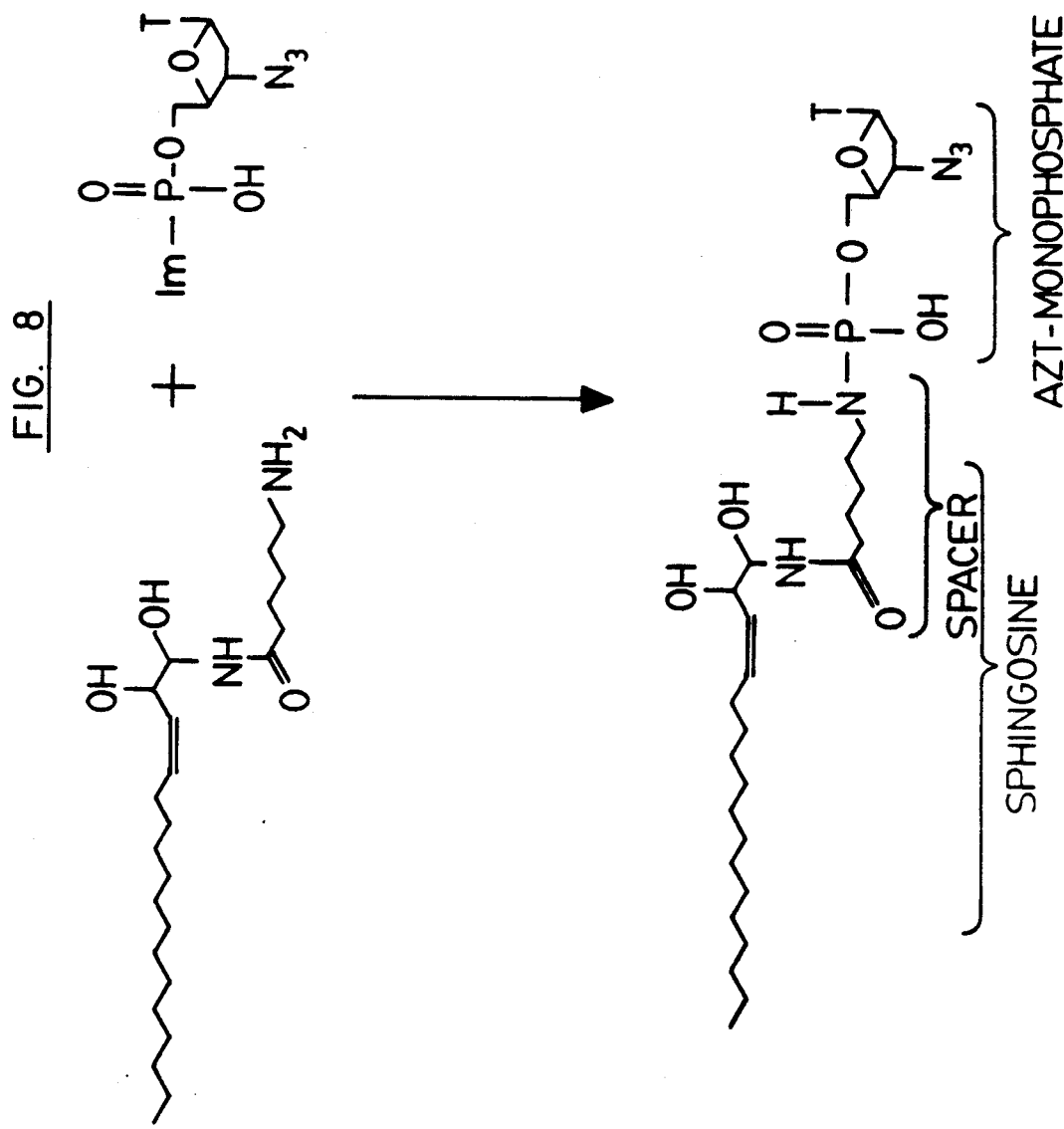
FIG. 8 depicts the synthetic scheme put forth in Example 8.

The present invention provides a method for facilitating drug entry into cells and for delivering drugs selectively to intracellular organelles. This is achieved by conjugating the desired therapeutic agent to a lipid carrier and administering this conjugate by standard techniques, including topical application.

The activity of these conjugates can be further refined by attaching the lipid carrier to a therapeutic agent through a spacer group having a first and a second end. Specifically, this is achieved through first linking the lipid to the first end of the spacer group through a linker functional group. In such a case, the therapeutic agent is then bound to a second end of the spacer group through a second linker functional group. This lipid/spacer/drug conjugate will provide enhanced flexibility and versatility in targeting drug delivery and in facilitating drug release upon reaching the target site.

Experimentally, it was found that the distribution of fluorescent ceramide is markedly different in neoplastic and virally infected cell lines as compared to "normal" cells. The marked difference in the distribution of fluorescent ceramide suggests that the neoplastic and virally infected cells have compromised golgi. Cells with compromised golgi could be made more susceptible to inactivation by treating them with ceramide linked to therapeutic agents which would direct them within the cell to the golgi.

A drug, as used herein, will be defined as including, but not necessarily limited to any anti-viral, antineoplastic drug. For the purposes of this application, compound 8, as referred to herein, is defined as the HIV1 protease inhibitor identified as compound 8 in Dreyer, G. B., et. al., *Inhibition of Human Immunodeficiency Virus 1 Protease Inhibitor In Vitro*. Rational design of substrate analog inhibitors PNAS Vol. 86, pp. 9752–56, Dec. 1986.

A lipid carrier, as defined herein will be taken to mean any lipid having an affinity for, or capable of crossing, a biological membrane, including but not limited to ceramide, phophatidyl choline, phosphatidic acid, estrogen, ether lipids, sphingomyelin or other sphingolipids.

A linker functional group is defined as any functional group for covalently binding the lipid carrier or therapeutic agent to the spacer group. These groups can be designated either "weak" or "strong" based on the stability of the covalent bond which the linker functional group will form between the spacer and either the lipid carrier or the drug. The weak functionalities include, but are not limited to phosphoramide, phosphoester, carbonate, amide, carboxyl-phosphoryl anhydride, ester and thioester. The strong functionalities include, but are not limited to ether, thioether, amine, amide and ester. The use of a strong linker functional group between the spacer group and the drug will decrease the rate at which the drug will be released at the target site, whereas the use of a weak linker functional group between the spacer group and the drug may act to facilitate release of the drug at the target site. Enzymatic release is another possibility, however, the rate of release of the drug would not necessarily be correlated with bond strength.

A spacer group may be broadly defined as any chemical group designed to facilitate the attachment of the drug/lipid conjugates to a target cell and/or the release of the drug at the desired target site. Such spacers may, facilitate enzymatic release at certain intracellular sites. Some spacers may simply present an "unhindered inhibitor," still linked to the carrier-spacer conjugate, to a target enzyme. Spacer groups, as described herein, include, but are not limited to aminohexanoic acid, polyglycine, polyamides, polyethylenes, and short functionalized polymers having a carbon backbone which is one to about twelve carbon molecules in length. Throughout the description of the examples, it will be assumed that all intermediate compounds will be isolated using standard methods.

EXAMPLE 1

An antiviral compound consisting of sphingosine conjugated to compound 8. Sphingosine is reacted with 1,3 Bis(trimethylsilyl)urea as described in W. Verbloom et al., 1981, Synthesis 807 to give a trimethyl silyl derivative of sphingosine. The sphingosine derivative is then conjugated with compound 8 in which the terminal amine is covered by a tBoc protecting group in the presence of diethyl azodicarboxylate (DEAD) and triphenyl phosphine as described in Y. Kishimoto, (1975), Chemistry and Physics of Lipids, 15:33–36. The sphingosine/compound 8 conjugate is then reacted in the presence of pyridine hydrofluoride as described in Matsuura, S. et al., (1976): J. Chem. Soc.-Chem. Communications, pg. 451., to remove the tBoc protecting group, to give compound 8 covalently bound to sphingosine through an amide bond.

EXAMPLE 2

An antiviral compound consisting of ceramide conjugated to a first end of a polyglycine spacer through an ester linker functional group, wherein enzyme inhibitor compound 8 is conjugated through an amide linker functional group to a second end of the polyglycine spacer. Polyglycine, as used in this example, has both a carboxy terminus and an amino terminus, the amino terminus being protected by a t-Boc group. Polyglycine is conjugated through its carboxy terminus to ceramide forming an ester linkage, as described in Anderson et al., 1963, J. Chem. Soc.-Chem. Communications, 85:3039. The resulting compound is further conjugated through the amino terminus of the polyglycine residue. Compound 8 has a carboxy terminus and an amino terminus. In this example the amino terminus is protected by a t-Boc protecting group. The conjugation takes place between the amino terminus of the polyglycine and the carboxy terminus of the HIV-1 protease inhibitor. This reaction is carried out in the presence of DEAD and triphenyl phosphine according to the method of Y. Kishimoto, (1975), Chemistry and Physics of Lipids, 15:33–36. The amino terminus of the HIV-1 protease inhibitor residue is deprotected according to the method of Matsuura, S. et al, 1976, J. Chem. Soc.-Chem. Communications, pg. 451.

EXAMPLE 3

An antiviral compound consisting of ceramide conjugated to AZT-monophosphate. Ceramide is reacted with AZT-monophosphate in the presence of dicyclohexylcarbodiimide as described in Smith, M. and Khorana, G.(1958), J.A.C.S. 80:1141 to yield ceramide conjugated through a phosphodiester bond to AZT-monophosphate.

EXAMPLE 4

An antineoplastic compound wherein sphingosine is conjugated through a phosphodiester bond to 5-fluorodeoxyuridine. Sphingosine is reacted with 5-fluorodeoxyuridine in the presence of dichlorophenyl phosphate according to the method of Baer 1955, Can. J. Biochem. Phys. 34:288, to yield sphingosine conjugated to 5-fluorodeoxyuridine through a phosphodiester bond.

EXAMPLE 5

An antiviral compound wherein ceramide is first conjugated to a first end of an oligomer 3 hydroxy propanoic acid spacer through an ester functional group, and wherein AZT is conjugated to a second end of said polyester spacer through a phosphodiester bond. First a polyester spacer is obtained, having a carboxyl at a first end and a triphenylmethyl group esterified to a second end. This spacer is conjugated to ceramide at its first end through an ester functional linker group according to the method of Anderson et al., 1963, J.A.C.S., 85:3039. This compound is then conjugated through the second end of the spacer compound to AZT monophosphate by means of a phosphodiester bond according to the method of Baer 1955, Can. J. Biochem. Phys. 34:288. In this antiviral compound, the bond breakage between the spacer and the drug would be slow in the absence of a phosphohydrolase.

EXAMPLE 6

An antiviral compound wherein phosphatidic acid, phosphatidyl choline, phophatidyl glycerol or phosphatidyl ethanolamine is linked through a phosphoester linker functional group to AZT. Phosphatidic acid, phosphatidyl choline, phophatidyl glycerol or phosphatidyl ethanolamine is conjugated to azido deoxythymidine according to the method of Baer et al., 1955.

EXAMPLE 7

An antiviral compound wherein ceramide is conjugated through an ester functional group to a first end of a polyglycine spacer, and wherein AZT is conjugated through a phosphoester functional group to a second end of the polyglycine spacer. Ceramide is first conjugated through an ester functional group to a first end of a polyglycine spacer (as described in Example 2). The ceramide-polyglycine compound is then conjugated through a phosphoester bond to a second end of the polyglycine spacer to AZT monophosphate according to the method of Paul, R., and Anderson, G. W., 1960, J.A.C.S. 82:4596.

EXAMPLE 8

An antiviral compound wherein aminohexanoyl sphingosine is conjugated to AZT. Aminohexanoyl sphingosine is conjugated with AZT monophophoimidazole according to the method of Paul, R., and Anderson, G. W., 1960, J.A.C.S. 82:4596 to yield aminohexanoyl sphingosine conjugated to AZT through a phophoramide bond.

What is claimed is:

1. A composition of matter comprising an antiviral or antineoplastic drug, a polar lipid carrier, two linker functional groups and a spacer, wherein the spacer has a first end and a second end and wherein the polar lipid is attached to the first end of the spacer through a first linker functional group and the antiviral or antineoplastic drug is attached to the second end of the spacer through a second linker functional group.

2. A composition of matter according to claim 1 wherein the spacer allows the drug to act without being released at an intracellular site and wherein the first linker functional group attached to the first end of the spacer is strong and the second linker functional group attached to the second end of the spacer is weak.

3. A composition of matter according to claim 1 wherein the spacer allows the drug to facilitate hydrolytic release of the drug at an intracellular site and wherein the first linker functional group attached to the first end of the spacer is strong and the second linker functional group attached to the second end of the spacer is weak.

4. A composition of matter according to claim 1 wherein the spacer allows the drug to facilitate enzymatic release of the drug at an intracellular site and wherein the first linker functional group attached to the first end of the spacer is strong and the second linker functional group attached to the second end of the spacer is weak.

5. A composition of matter according to claim 1 wherein the polar lipid is sphingosine, ceremide, phosphatidyl choline, phosphatidyl glycerol, phosphatidyl ethanolamine or phosphatidic acid.

6. A composition of matter according to claim 1 wherein the spacer is a peptide of formula$_n$, wherein n is an integer between 2 and 25, and the peptide comprises a polymer of a particular amino acid.

7. A composition of matter comprising an antiviral or antineoplastic drug having a first functional linker group, and a polar lipid carrier having a second functional linker group, wherein the antiviral or antineoplastic drug is covalently linked to the polar lipid carrier by a chemical bond between the first and second functional linker groups.

8. A composition of matter according to claim 7 wherein the first functional linker group is a hydroxyl group, a primary or secondary amino group, a phosphate group or substituted derivatives thereof or a carboxylic acid group.

9. A composition of matter according to claim 7 wherein the second functional linker group is a hydroxyl group, a primary or secondary amino group, a phosphate group or substituted derivatives thereof or a carboxylic acid group.

10. A composition of matter according to claim 7 wherein the polar lipid is sphingosine, ceremide, phosphatidyl choline, phosphatidyl glycerol, phosphatidyl ethanolamine or phosphatidic acid.

* * * * *